United States Patent [19]

Pirklbauer et al.

[11] Patent Number: 5,234,200
[45] Date of Patent: Aug. 10, 1993

[54] METHOD AND ARRANGEMENT FOR PREVENTING CRUSTS FROM AGGLOMERATION IN A METALLURGICAL VESSEL

[75] Inventors: Wilfried Pirklbauer, Niederneukirchen; Norbert Ramaseder, Linz; Johannes Steins, Gallneukirchen, all of Austria

[73] Assignee: Voest-Alpine Industrieanlagenbau GmbH, Linz, Austria

[21] Appl. No.: 987,570

[22] Filed: Dec. 8, 1992

Related U.S. Application Data

[63] Continuation of Ser. No. 791,015, Nov. 12, 1991, abandoned.

[30] Foreign Application Priority Data

Nov. 14, 1990 [DE] Fed. Rep. of Germany ....... 4036216

[51] Int. Cl.⁵ .............................................. C21B 7/24
[52] U.S. Cl. ...................... 266/44; 266/79; 266/99; 75/375; 75/376
[58] Field of Search .................. 75/375, 376; 266/44, 266/79, 99

[56] References Cited

U.S. PATENT DOCUMENTS

4,361,315  11/1982  Kajihara et al. ................ 266/99

FOREIGN PATENT DOCUMENTS

0162949  12/1985  Austria .
0364825  4/1990   Austria .
79290    5/1983   European Pat. Off. .
278217   12/1987  Japan ............................. 266/99

*Primary Examiner*—Melvyn J. Andrews
*Attorney, Agent, or Firm*—Hopgood, Calimafde, Kalil, Blaustein & Judlowe

[57] ABSTRACT

There are disclosed a method and an arrangement for preventing the agglomeration of crusts in a lance opening passing a wall of a metallurgical vessel and provided for a lance carrying a measuring and/or sampling probe. During the metallurgical process proceeding within the metallurgical vessel and during the taking of a measurement and/or sample by means of a lance introduced into the metallurgical vessel through the lance opening, a gas that is inert relative to a melt bath contained in the metallurgical vessel, or air, is injected into the lance opening from outside, which gas produces a gas veil at the mouth of the lance opening facing the melt bath.

6 Claims, 2 Drawing Sheets

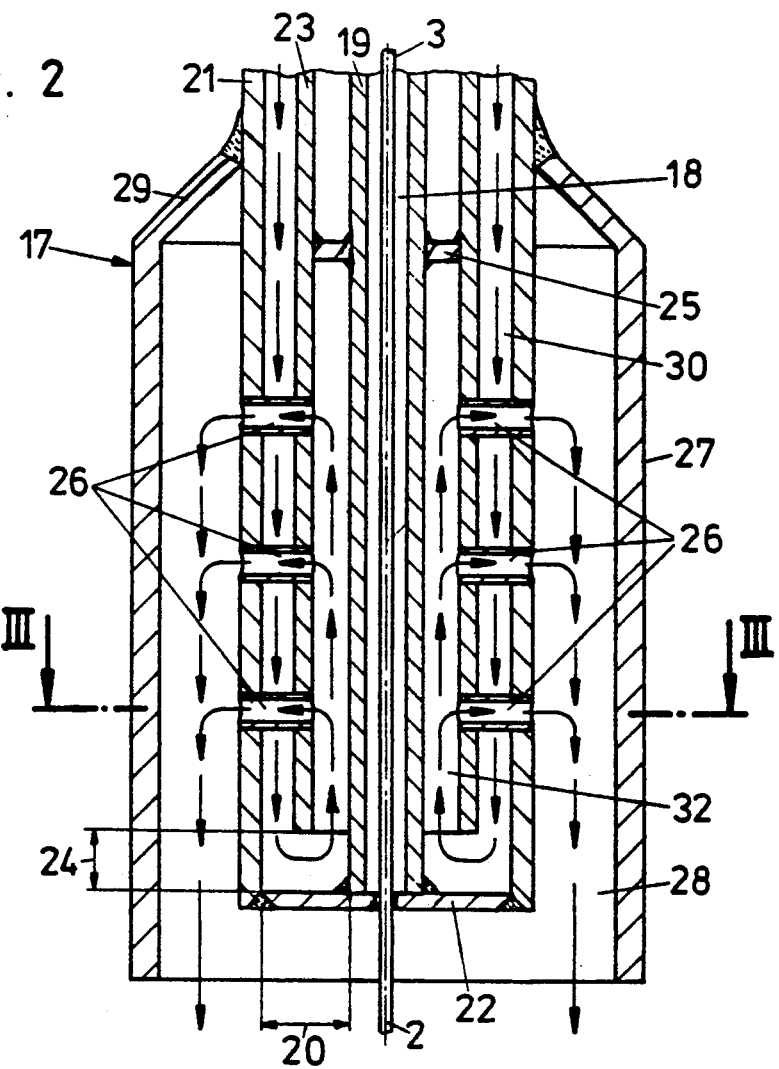
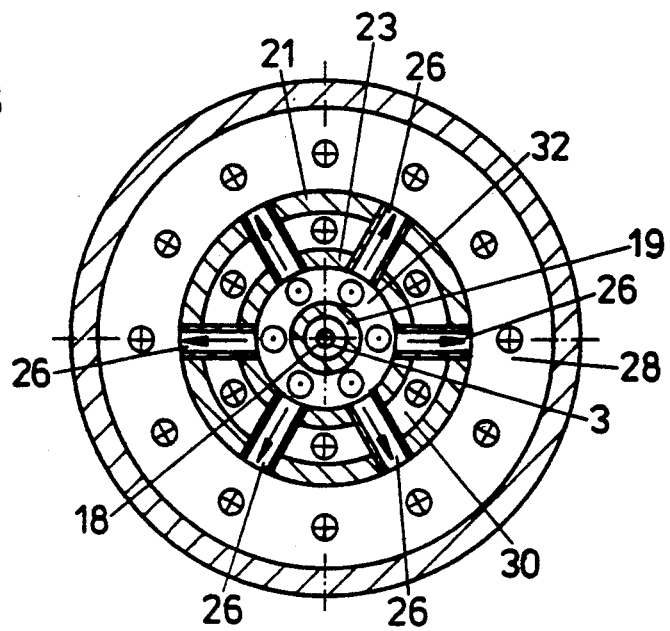

METHOD AND ARRANGEMENT FOR PREVENTING CRUSTS FROM AGGLOMERATION IN A METALLURGICAL VESSEL

This application is a continuation of application Ser. No. 791,015, filed Nov. 12, 1991 now abandoned.

The invention relates to a method of preventing the agglomeration of crusts, in particular of slag crusts, in a lance opening passing a wall of a metallurgical vessel and provided for a lance carrying a measuring and/or sampling probe, as well as to an arrangement for realizing this method.

It is known (EP-A1 0 079 290) to provide a lance opening at a converter, which penetrates the wall of the converter in the upper third of the wall near its mouth. A lance equipped with a measuring or sampling probe is introducible or removable through this lance opening. Such a separate lance opening is suitable if the mouth of the converter is only difficult to accede.

In practice, lance openings of this type have proved to grow together again and again, since slag agglomerates there, forming particularly stable compounds with the refractory lining of the converter. Removal of such agglomerations is feasible only by boring open the lance opening, which frequently causes damage to the lining of the metallurgical vessel and also is very time-consuming. However, since measurements are to be carried out as rapidly as possible, it is particularly disadvantageous if cleaning a lance opening prior to taking a measurement is feasible only with difficulty.

The invention aims at avoiding these disadvantages and difficulties and has as its object to provide a method of the initially defined kind and an arrangement for realizing this method, which prevent crusts from growing together or agglomerating at the lance opening such that it is possible to take a measurement or a sample at any time and without impediment, even during the blowing procedure.

In accordance with the invention, this object is achieved in that, during the metallurgical process proceeding within the metallurgical vessel and during the taking of a measurement and/or sample by means of a lance introduced into the metallurgical vessel through the lance opening, a gas that is inert relative to a melt bath contained in the metallurgical vessel, or air, is injected into the lance opening from outside, which gas produces a gas veil at the mouth of the lance opening facing the melt bath.

The method according to the invention may be employed with particular advantage in the production of steel in a basic oxygen steelworks converter, the inert gas or air being injected into the lance opening during the blowing procedure.

Preferably, nitrogen in an amount of less than 4 Nm$^3$/min is injected as the inert gas.

An arrangement for realizing this method with a metallurgical vessel comprising a lance opening penetrating its wall is characterized in that a bell-shaped gas conducting means having its cross section adapted to the cross section of the lance opening is insertable into the lance opening and is connected to a gas feed for inert gas or air, whose open end is directed towards the inside mouth of the lance opening and which has an axial throughhole, through which a lance carrying a measuring and/or sampling probe is movable.

In order to facilitate the introduction of the lance, a tubular lance guide suitably is adapted to be positioned between the bell-shaped gas conducting means and the lance opening, projecting into the lance opening from outside and being displaceable relative to the lance opening.

A preferred embodiment is characterized in that the bell-shaped gas conducting means comprises a central tube that constitutes the axial throughhole for introducing the lance and is surrounded by an external tube at a peripheral distance, an intermediate tube is inserted between the external and central tubes, the external tube is connected to the central tube by means of an annular bottom plate closing the annular space between the external and central tubes, the intermediate tube ending at a distance above the bottom plate, a detent ring is provided between the intermediate tube and the central tube, closing the annular space between the same and being arranged at a distance from the bottom plate, several radially directed gas passages are provided between the intermediate tube and the external tube between the bottom plate and the detent ring in terms of height, furthermore, the external tube is surrounded by a bell-shaped sleeve tightly following upon the external tube by a distance from the bottom plate such that a further annular gas space is formed between the external tube and the sleeve, into which the gas passages enter and which is outwardly open towards the end comprising the bottom plate.

In the following, the invention will be explained in more detail by way of an embodiment illustrated in the accompanying drawings, wherein:

FIG. 2 is an axial section through an arrangement according to the invention on an enlarged scale as compared to FIG. 1; and FIG. 3 represents a section along line III—III of FIG. 2.

Figure 1:
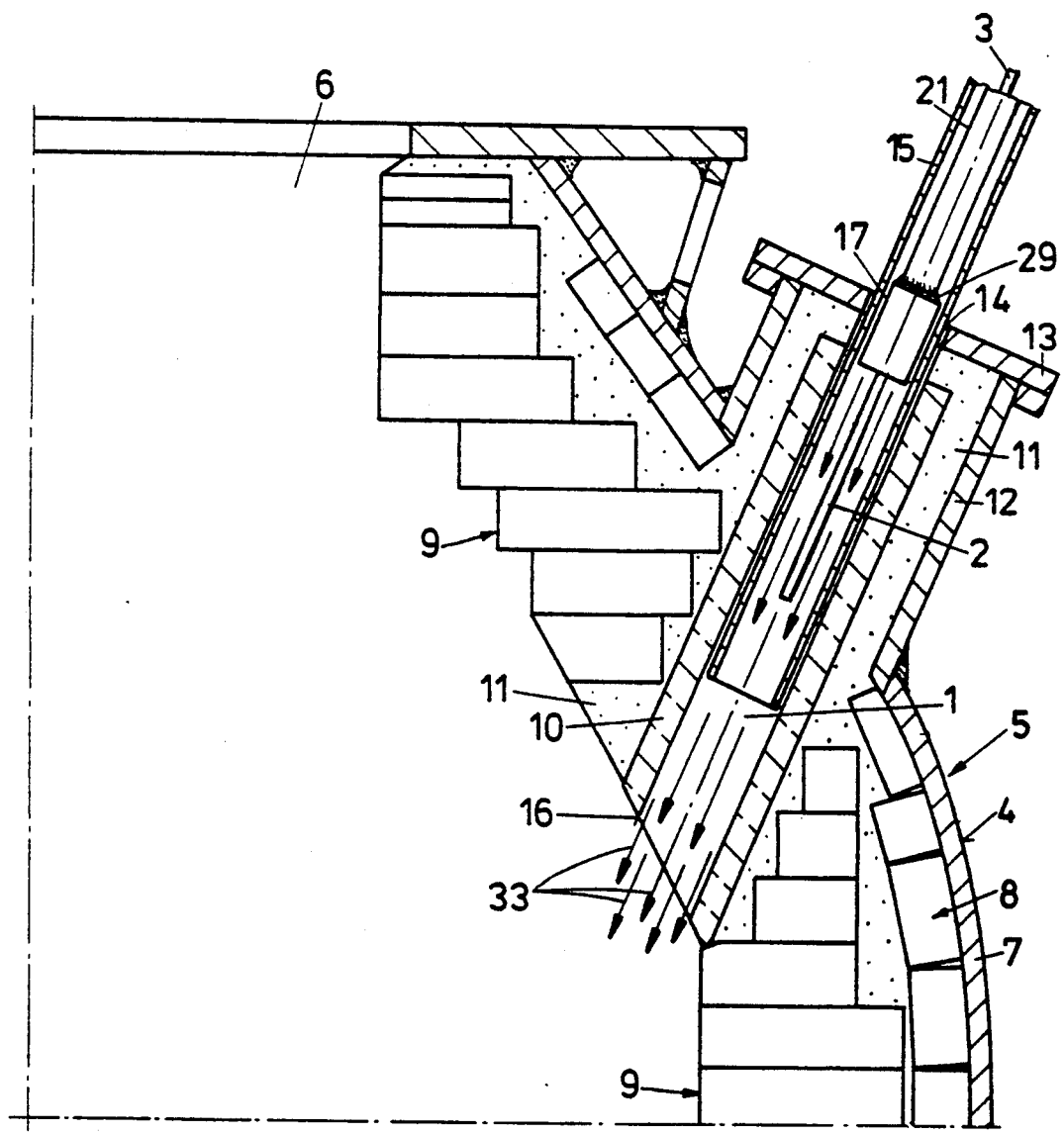
FIG. 1 is a partial section through a steelworks converter whose plane of section has been laid through the axis of rotation of the steelworks converter.

As is apparent from FIG. 1, a lance opening 1 for introducing and removing a lance 3 equipped with a measuring and/or sampling probe 2 penetrates the wall 4 of a steelworks converter 5 in the vicinity of its mouth 6. The wall 4 of the steelworks converter 5 is comprised of a shell 7 of steel, to whose internal side a permanent lining 8 is attached. The permanent lining 8 is covered by a refractory working lining 9. In the region of the lance opening 1, a hollow cylinder 10 of refractory material is provided, which is fixed in the brickwork by monolithic lining material 11.

In the region of the lance opening 1, the wall 4 of the converter 5 comprises a socket 12 of steel having a flange-likely projecting end plate 13. The hollow cylinder 10 projects into the socket 12 as far as to closely in front of the end plate 13. In the end plate 13, a bore 14 is provided in alignment with the lance opening 1, through which a tubular lance guide 15 is insertable into the interior of the hollow cylinder 10, as is apparent from FIG. 1. The front end of the tubular lance guide is located at a distance from the inside mouth 16 of the same, which approximately amounts to one third of the length of the lance opening 1.

A bell-shaped gas conducting means 17, which is adapted with its cross section to the cross section of the lance opening 1 and to that of the lance guide 15, is introducible into the lance guide 15. The structure of the gas conducting means 17 is illustrated in detail in FIGS. 2 and 3. The gas conducting means 17 comprises an axial hole 18 formed by a central tube 19 for introducing the lance 3, which serves to take a measurement and/or a sample.

This central tube 19 is surrounded by an external tube 21 at a peripheral distance 20 and is tightly connected to the external tube 21 on the front end by means of an annular bottom plate 22. Between the central tube 19 and the external tube 21, an intermediate tube 23 is inserted, ending at a distance 24 above the bottom plate.

A detent ring 25 is welded between the intermediate tube 23 and the central tube 19, upwardly closing the space between these two tubes. This detent ring 25 is arranged at a distance from the bottom plate 22. Several radially directed gas passages 26, by which the intermediate tube 23 communicates with the external tube 21, are each provided at different levels above the bottom plate 22 and below the detent ring 25.

A bell-shaped sleeve 27 follows upon the external tube 21 approximately at the height of the detent ring 25, forming an annular gas space 28 relative to the external tube 21, which is open downwardly, i.e., in the direction towards the bottom plate 22, and which is closed in the opposite direction by a constriction 29 of the sleeve 27, by means of which the sleeve 27 is welded to the external tube 21. This sleeve 27 covers all the radially oriented gas passages 26.

The arrangement functions in the following manner:

Inert gas, such as, for instance, nitrogen, or compressed air is injected in an amount of less than 4 $Nm^3$/min through the annular gas space 30 formed by the intermediate tube 23 and the external tube 21. The gas flow is deflected in the region of the bottom plate 22 such that the gas streams into the annular space 32 formed between the central tube 19 and the intermediate tube 23. From there, it gets into the annular gas space 28 provided between the bell-shaped sleeve 27 and the external tube 21, via the radially directed gas passages 26, through which gas space 28 it streams towards the converter interior. Thus, a gas veil 33 is formed at the vessel inside mouth 16 of the lance opening 1, reliably preventing the agglomeration of slag.

The lance 3 equipped with a measuring and/or sampling probe 2 can be introduced into the converter 5 during the blowing procedure while maintaining the gas veil 33 of inert gas without the measurement or sampling being impeded by any agglomeration whatsoever formed at the lance opening 1.

Due to the gas veil 33 produced at the inside mouth 16 of the lance opening, cumbersome cleaning of the lance opening is saved. In addition, the provision of a stopper for closing the lance opening 1 can be obviated. Moreover, the gas veil 33 offers an intensive probe cooling to the lance placed in the stand-by position despite a very slight gas consumption such that a good contact between the measuring probe 2 and the lance 3 carrying the measuring probe 2 will always be safeguarded, measuring errors thus being avoided.

What we claim is:

1. A method of preventing crusts from agglomerating in a lance opening passing the wall of a metallurgical vessel containing a melt bath, for introducing into the metallurgical vessel a measuring and/or sampling probe-carrying lance having a lance opening mouth facing said melt bath, which method comprises injecting a gas selected from the group consisting of a gas inert relative to said melt bath contained in the metallurgical vessel and air, from outside into said lance opening through said lance while carrying out a metallurgical process within the metallurgical vessel and while taking a measurement and/or sample by said lance introduced into said metallurgical vessel through said lance opening, said gas forming a gas veil at said lance opening mouth facing said melt bath.

2. The use of the method set forth in claim 1 in an oxygen blowing converter for the production of steel to prevent slag crusts from agglomerating during the production of steel, wherein said gas is injected into said lance opening during blowing.

3. A method as set forth in claim 2, wherein said inert gas is comprised of nitrogen in an amount of less than 4 $Nm^3$/min.

4. For use in a metallurgical vessel having a vessel wall and a lance opening penetrating said vessel wall and adapted to introduced into said metallurgical vessel a measuring and/or sampling probe-carrying lance having an inside lance opening mouth, an arrangement for preventing crusts from agglomerating in said lance opening by injection of a gas-veil-forming gas selected from the group consisting of a gas inert relative to said melt bath contained in the metallurgical vessel and air, which arrangement comprises a bell-shaped gas conducting means having a cross section adapted to the cross section of said lance opening and insertable into said lance opening, a gas feed means adapted to supply said gas and having its open end directed to said inside lance opening mouth, said gas conducting means being connected to said gas feed means, and said gas feed means having an axial throughhole for said measuring and/or sampling prob-carrying lance to be moved therethrough.

5. An arrangement as set forth in claim 4, further comprising a tubular lance guide adapted to be positioned between said bell-shaped gas conducting means and said lance opening, said tubular guide projecting into said lance opening from outside and being displaced relative to said lance opening.

6. An arrangement as set forth in claim 5, wherein said bell-shaped gas conducting means includes a central tube consisting said axial throughhole for introducing said lance and an external tube surrounding said central tube at a peripheral distance by forming a first annular space therebetween, and further comprising an intermediate tube inserted between said external tube and said central tube by forming a second annular space between said central tube and said intermediate tube, an annular bottom plate provided to connect said external tube with said central tube and to close said first annular space, said intermediate tube ending at a distance above said bottom plate, a detent ring arranged between said intermediate tube and said central tube at a distance from said bottom plate for closing said second annular space, several radially directed gas passages provided between said intermediate tube and said external tube between said bottom plate and said detent ring in terms of height, a bell-shaped sleeve tightly following upon said external tube by a distance from said bottom plate and surrounding said external tube in a manner so as to form a third annular space for gas between said external tube and said sleeve, said third annular space being externally open towards the end comprising said bottom plate and receiving said gas passages.

* * * * *